United States Patent [19]
Moore et al.

[11] 4,014,208
[45] Mar. 29, 1977

[54] ULTRASONIC SYSTEM FOR MEASURING DIMENSIONAL OR STRESS CHANGE IN STRUCTURAL MEMBER

[75] Inventors: John F. Moore, Marina del Rey; Forrest M. Coate, Hawthorne, both of Calif.

[73] Assignee: Rockwell International Corporation, El Segundo, Calif.

[22] Filed: Apr. 1, 1976

[21] Appl. No.: 672,692

[52] U.S. Cl. .................................. 73/67.9; 73/88 F
[51] Int. Cl.² ........................................ G01N 29/00
[58] Field of Search ............ 73/67.2, 67.7, 67.8 R, 73/67.9, 95, 88 F

[56] References Cited
UNITED STATES PATENTS

| | | | |
|---|---|---|---|
| 3,427,868 | 2/1969 | Charbonnier et al. | 73/67.9 |
| 3,759,090 | 9/1973 | McFaul et al. | 73/67.9 |
| 3,918,294 | 11/1975 | Makino et al. | 73/67.2 |

*Primary Examiner*—James J. Gill
*Attorney, Agent, or Firm*—Charles T. Silberberg; L. Lee Humphries

[57] ABSTRACT

An ultrasonic system for measuring dimensional change in a structural member, and particularly change in a fastener due to tensile stress, utilizes means for double pulsing a transducer to transmit an acoustic pulse into the member at one end for reflection from its other end with a period between paired pulses selected to cause the second echo received of the first pulse to coincide with the first echo of the second pulse. A VCO is employed with a digital counter to time the period between paired pulses, the interval between successive paired pulses, and the time of a predetermined number of pulse pairs. The latter timing is used to alternatively shift the frequency of the VCO high and low to cause the first echo of the second pulse to be offset in phase from the coincidence position it might have at the central frequency. Phase detection and integration of the echo pulse coincidence during alternately high and low frequency offsets produces a phase-sensitive feedback signal to the VCO to drive its central frequency toward precise coincidence. Comparing the central frequency, $f$, with an initial frequency, $f_o$, for the unstressed condition of the member yields a measurement of its stress. The change $(f_o - f)$ is compared with a predetermined value, $\Delta f$, while stressing in order to adjust stress to that value. Initial and final conditions may be stored for comparison with subsequent stress measurement data.

18 Claims, 4 Drawing Figures

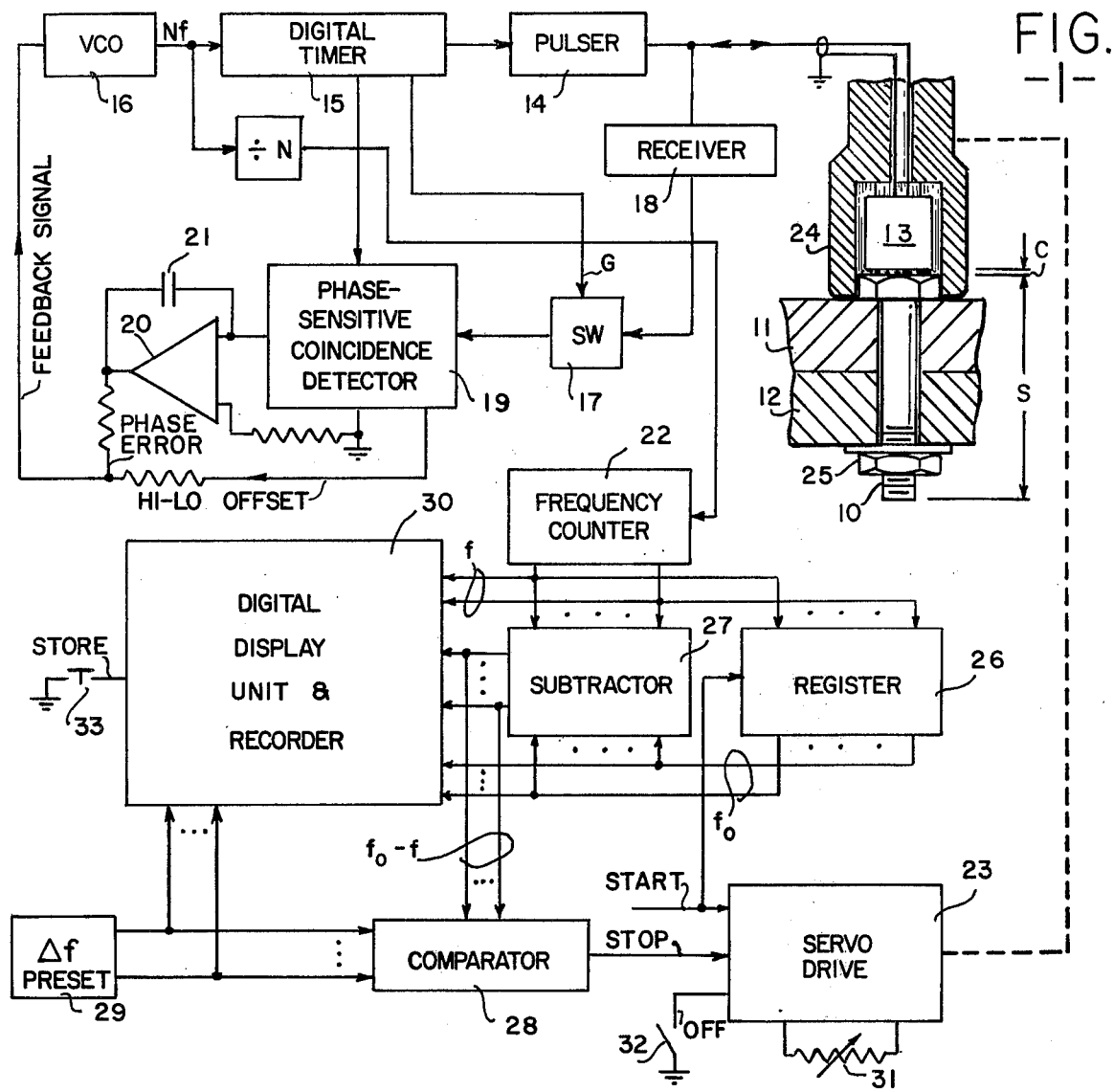
FIG. -1-
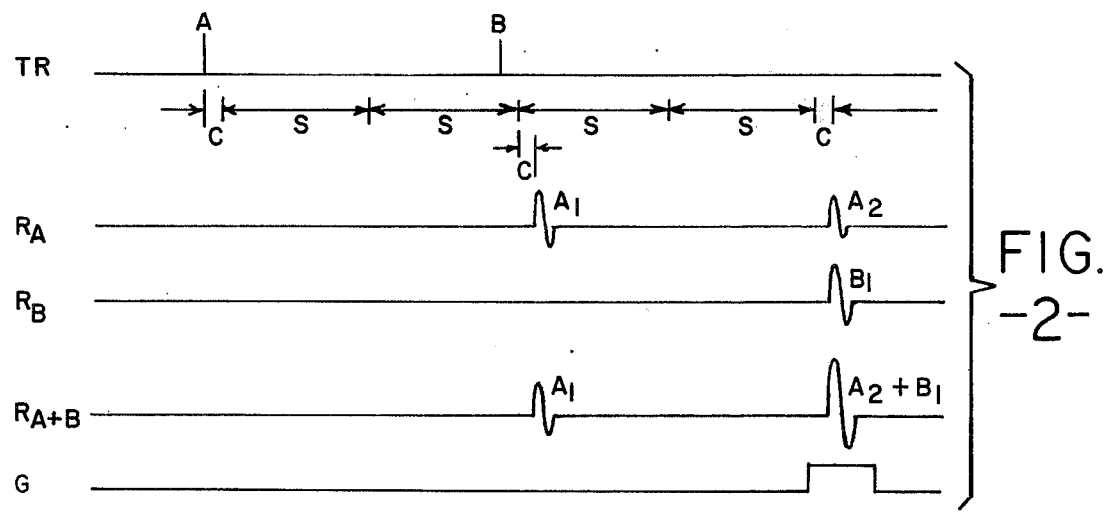
FIG. -2-

ULTRASONIC SYSTEM FOR MEASURING DIMENSIONAL OR STRESS CHANGE IN STRUCTURAL MEMBER

BACKGROUND OF THE INVENTION

This invention relates to a method and apparatus for non-destructively determining dimensional changes in a member, such as changes due to stresses or thermal expansion in structural members, or structural loads in buildings, bridges and the like, and even in machining, grinding, polishing or otherwise processing of a member.

An urgent need exists within many industries for a low cost precision method of installing structural members subject to stress particularly in high risk fracture control structures. The requirements for such a method are stringent and must account for a number of different types of structural members and installation conditions. In addition the method should be capable of both production line and field use. Further, the method should be capable of providing for repeat inspections with the information of previous inspections stored and retrieved for evaluating the effect of complex installation procedures and service load conditions.

A successful development of such a method requires the solution to a number of interrelated problems. For instance, the desired stress load to be controlled is the actual stress load existing in the member as opposed to other frictional or installation loads developed by the installation conditions, e.g., alignment effects, countersinks, surface roughness, etc. The interaction of these conditions on the load is extremely complex and must be analyzed to determine the effect on the actual stress load in the member. Additionally, the material characteristics of the structural system (fasteners, nut, washer, spacers) including physical properties (modulus, density, etc,.) and geometric properties (size, tolerances, surface roughness, etc.) could significantly affect the accuracy and reliability of the load measuring method.

There are two nondestructive test methods that have been developed for determining stresses in metal members. These methods are X-ray diffraction and ultrasonics. X-ray diffraction techniques, which measure changes in the lattice spacing in known crystal systems require removal of material, and limitations are placed on the member geometry and the state of stress to be measured. Ultrasonic techniques measure the travel distance and the velocity of ultrasonic waves propagating in a member which is affected by the magnitude of the applied stress in the member.

An ultrasonic method is considered the most direct and accurate method for accurately measuring and controlling fastener load for the following reasons: the ultrasonic measurement is directly relatable to the tensile load in the fastener; the measurement is independent of the variable section modulus of the clamped structure and the "friction effects" caused by imperfect action between the fastener and nut; and very importantly, measurements can be made at any time in the life of the fastener without changing or affecting the load on the fastener. Some or all of these considerations are also applicable to other types of structural members.

Various systems using an ultrasonic method have been proposed for measuring tensile load in a fastener. Such a system disclosed in U.S. Pat. No. 3,759,090, titled Ultrasonic Extensometer, employs circuit means for analog measurement and display of a delay in receiving an echo pulse from the far end of a fastener. A complex system of multivibrators includes a vernier multivibrator employed to gate an oscillator on to produce periodic pulses at a fixed rate for an extended period from a time after the ultrasonic pulse has entered the fastener to a time after the echo pulse is received. The received echo pulse sets a timing multivibrator, and the next one of the vernier periodic pulses resets the timing multivibrator. The duration of the resulting output pulse from the timing multivibrator will decrease as the fastener is decreased in length (loosened) and increase as the fastener is increased in length (tightened). For ease of operation, the vernier multivibrator is set to produce adjacent periodic pulses spaced equal time intervals from an echo pulse. The output pulse of the timing multivibrator will then yield a pulse width modulated output proportional to the change in fastener length. Each output pulse is converted from pulse width to pulse height for display purposes.

The problem with such a system is that it relies upon the stability of multivibrators for timing, and therefore readjustment of the multivibrators each time it is used. Since it yields only change in length information when the system is used, it cannot provide length data that may be stored for comparison with tests made at a later date to determine if the fastener has undergone changes in stress. The system will provide data only on change in stress at the time the fastener is beng tightened or loosened. This method is also dependent on transit time through the coupling system and is subject to inaccuracies due to coupling variations during application of loads. Periodic maintenance tests on the stress of the fastener are not possible.

Another approach to measuring load stress (length) of a fastener is based upon the change in resonant frequency that a fastener undergoes due to any change in length. While this distinct approach utilized in the systems disclosed in U.S. Pat. Nos. 3,306,100 and 3,307,393 is capable of providing data on the absolute length of the fastener, as opposed to only change in length, the fastener is damped by the structural members being fastened, i.e., the true resonant frequency of the member is changed by coupling with fastened members. It is therefore believed that an ultrasonic pulsing technique will provide superior results as compared to any mechanical vibration technique.

Process monitoring of machining, grinding, polishing or other material processing of a member is desirable to determine precise amount and/or rate of material removal. The monitoring system should provide in-process real-time measurement and data for control of equipment performing the process. In addition, accurate certification of final material dimension(s) eliminates normal quality control inspection function. Such a monitoring system would provide more accurately processed material, thus producing savings from: eliminating the possibility of over processing material; more efficient processing to reduce total time; and saving inspection time by providing certified thickness data.

As steel framed buildings, bridges and the like are constructed, the loads in the structural members, such as "I" beams and other members, are equalized by adjustment of struts and braces. The compressive loads in the structural members as well as the tensile loads in the struts and braces should be monitored during installation, and in many cases during periodic inspection to assure proper construction, and could also be used for periodic checks to detect shifts or relaxation, and to study the effects of earthquakes and strong winds.

OBJECTS AND SUMMARY OF THE INVENTION

An object is to provide a method and apparatus for measuring the ultrasonic transit time of a pulse through a structural member without regard to the transit time through coupling media.

Another object of this invention is to provide an improved method and apparatus for measuring dimensional change of a structural member.

Still aother object is to provide an improved method and apparatus for measuring stress on a member during installation or preloading of the member as well as during any inspection required subsequent to installation for the purpose of detecting any change in stress without affecting the stress during such an inspection. For that purpose, provision is made to store test data for determining change in stress from one inspection to the next.

These and other objects and advantages of the present invention are achieved by double pulsing an ultrasonic transducer coupled to a structural member at a rate (periodic between paired pulses) so adjusted that the second reflected echo of the first pulse of a pair coincides with the first reflected echo of the second pulse of the pair. The pulse rate so adjusted is an accurate measure of the round trip transit time of a ultrasonic pulse through the member, and therefore its dimension in the direction of the ultrasonic pulse transmission. A member undergoing stress will change in length by an increment $\Delta L$ and in acoustic velocity by an increment $\Delta V$. Both increments will contribute to a change in transit time in proportions that may be predetermined theoretically and empirically. By continually adjusting the pulse rate while the member is being stressed, or is being processed to produce a dimensional change and stopping the stressing process at a predetermined transit time, the member may be preloaded at the time of installation with a degree of accuracy limited only by the accuracy with which the pulse rate can be adjusted for the first echo of the second pulse of a pair to coincide with the second echo of the first pulse of the pair. Thus it is possible to determine the transit time of a member before and after stressing to determine its ultimate stress load, and to periodically inspect the specimen to determine any change in stress by again measuring the round trip transit time of the member and comparing it with the transit time measured during installation or the last inspection. The same technique for measuring transit time will also permit in-process measuring of dimensional changes in a member undergoing some process that will change its dimension.

To increase the degree of accuracy with which the pulse rate is adjusted, a variable oscillator is employed to generate a signal at a frequency significantly greater than the frequency of a pulse pair. That signal is then frequency divided by counters to time the period between pulses of a pair, and to so time the period between pulse pairs as to permit energy from one pair to be substantially dissipated before the next pulse. The frequency of the oscillator is then adjusted to yield the desired coincidence in reflected pulses of a pulse pair. To achieve this coincidence, the frequency of the oscillator is alternately varied between incrementally higher and lower frequencies for a predetermined number of pulse pairs, thus varying the phase of the reflected pulses of the pulse pairs, and integrating the composite echo pulse signals received for the high and low frequencies. If the central frequency of the oscillator is too high, an integrated signal of one polarity is produced, and if central frequency is too low, an integrated error signal of opposite polarity is produced. This integrated error signal is employed to automatically adjust the oscillator so that the high and low frequencies produce equal and opposite phase errors in the desired coincidence between echoes in the successive pulse pairs. The central frequency of the oscillator will thus be a measure of dimensional change of the member at any given time. That frequency is measured and compared with a predetermined frequency for a desired dimensional change. Once the changing process has been stopped, the value of the central frequency is stored for comparison with measurements during a subsequent inspection, as for stress preloading and subsequent inspection without unloading and reloading.

The novel features of the invention are set forth with particularity in the appended claims. The invention will best be understood from the following description when read in conjunction with the accompanying drawings.

BRIEF DESCRIPTION OF THE DRAWINGS

FIG. 1 is a functional block diagram of a system embodying the present invention.

FIG. 2 is a timing diagram useful in understanding the underlying principles of the invention.

DESCRIPTION OF THE PREFERRED EMBODIMENTS

Figure 3:
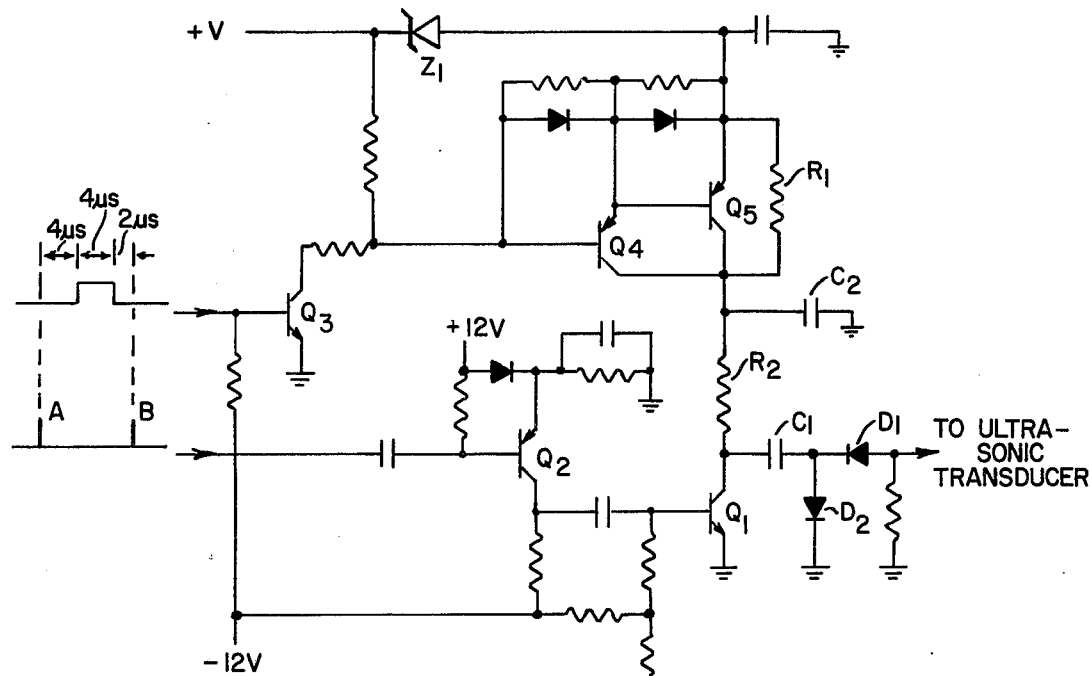
FIG. 3 is a diagram of a circuit for producing paired pulses at close intervals in the system of FIG. 1.

Referring now to FIG. 1, there is disclosed a system capable of measuring dimensional change of a structural member such as due to stress of a bolt 10, or any other type of fastener, fastening two plates 11 and 12. The system is also capable of measuring stress (tension or compression) of any other type of structural member, or any dimensional change of whatever cause, such as thermal expansion or material processing, as will become apparent from the following example of measuring tensile load in a bolt.

The system employs an ultrasonic transducer 13 coupled to the head of the bolt by a suitable coupling material of a thickness C, such as oil (or preferably a "dry coupler" material comprised of elastomeric materials as described in U.S. Pat. No. 3,663,842 dated 16 May 1972, titled THERMOPLASTIC ELASTOMER MATRIX DRY ACOUSTICAL COUPLE). The measurement system employs a unique double pulse technique that measures only the acoustic transit time within the structural member and is therefore relatively free of time variations attributable to changes in the acoustic coupling to the member, and of acoustic interference between reflected and refracted acoustic pulses within the member, a common fault in other ultrasonic systems. Standard types of fasteners commonly used in the aircraft industry have been load tested with an accuracy of about 3% at a 95% confidence limit, and of about 4% at a 99% confidence limit. That compares very favorably with torque measurement systems for bolts where the error is about 18% at a 95% confidence limit and about 27% at a 99% confidence limit. Thus the present invention provides a significant improvement over conventional torque methods for bolts, both during load application and as required subsequently for inspection, and the latter is without the need for unloading and reloading as in prior ultrasonic techniques due to the unique double pulse technique employed.

The organization of an exemplary embodiment will be described with references to FIGS. 1 and 2 before discussing underlying theoretical considerations and preferred circuits for the exemplary embodiment. A pulser 14 is triggered by a digital timer 15 driven by a voltage controlled oscillator (VCO) 16 to transmit paired ultrasonic pulses (A,B) through the bolt by the transducer. The timing of the second pulse, B, of a pulse pair is selected through control of the VCO to cause the first reflection $B_1$ of the second pulse B to coincide with the second reflection $A_2$ of the first pulse A as shown in FIG. 2, thus creating a maximum response when the echo pulses gated by a switch 17 from a receiver 18 are coincident, i.e., when the oscillator frequency yields coincidence. The digital timer 15, which times the pulser 14 also generates the gating pulse, G, applied to the switch 17 for a period spanning the expected time of the coincident echo (which depends upon the length of the member being stress tested), thereby minimizing interference from unwanted acoustic reflections.

The digital timer also times the operation of a phase-sensitive coincidence detector 19 to integrate the coincident pulses through a integrator comprising an operational amplifier 20 and feedback capacitor 21. The output of the integrator is employed as a feedback signal to adjust the frequency of the VCO to the length of the bolt with an offset introduced in the feedback signal that, for a predetermined time (e.g., five pulse pairs), will drive the VCO too high by a predetermined amount, and for an equal time will drive the VCO too low by the same amount, i.e., will drive the VCO above and below the central frequency by the same amount for alternate periods of equal duration. The result is that if the central frequency is too low, the offset feedback indicates the frequency of the oscillator is too low, and if the central frequency is too high, the offset feedback indicates the frequency of the oscillator is too high. Otherwise, the offset feedback alternates between too high and too low to hold the central frequency constant. This technique of purposely offsetting the feedback to the VCO avoids the problem of detecting when a maximum peak has been reached for coincidence in the second echo pulse $A_2$ of the first pulse A in a pair with the first echo pulse $B_1$ of the second pulse B of the pair.

The output of the VCO is measured by a frequency counter 22, which has its own stable clock to determine a predetermined period of counting, such as one second. That counting period is sufficiently long for a number of Hi-Lo cycles of the detector 19 to have been completed in order to provide an average (central) frequency over that period. After each frequency counting cycle, the central frequency value is gated into an output buffer register of the counter 22 as a measure of the bolt stress. Initially, frequency $f_o$ is gated into the output buffer for the unstressed bolt.

To tighten the bolt, a servo drive unit 23 is turned on by a START signal, as by the push of a button (not shown). The drive unit then torques a socket wrench 24 clockwise while a nut 25 is held steady by suitable means (not shown), such as a box wrench. As the bolt is tightened, the increasing tensile load will cause the effective length of the bolt to increase, causing the second echo return $A_2$ of the first pulse A of each pair to occur after the first echo return $B_1$ of the second pulse B. To restore coincidence, it is necessary to decrease the central frequency of the VCO. The process of continually decreasing the central frequency continues as the bolt is tightened.

When the servo drive unit 23 is turned on by the start signal, the initial frequency, $f_o$, then in the output buffer of the counter 22, is stored in a register 26. A subtractor 27 continuously provides the difference, $f_o - f$, to a comparator 28. When the difference reaches a preset value, $\Delta f$, set by suitable means 29, such as by thumb-wheel switches, the servo drive unit 23 is stopped. In practice, the comparator will not only determine when $f_o - f = \Delta f$ to stop the unit, but will also decrease the drive as $f_o - f$ approaches $\Delta f$ in order that the servo does not overdrive the socket wrench. This may be accomplished by implementing the comparator as a subtractor followed by a digital-to-analog converter that produces an error signal to the servo drive unit which decreases toward zero as the difference $(f_o - f) - \Delta f$ approaches zero. To assure adequate drive until the difference $(f_o - f) - \Delta f$ is within a predetermined range of zero, the digital-to-analog converter may be followed by an amplifier which saturates to produce a maximum error signal above that range, and a linearly decreasing error signal within that range with a slope empirically determined to bring the servo drive unit to rest with the stress on the bolt within the required tensile loading tolerance.

A digital display and recorder 30 stores the initial frequency $f_o$ for future reference, and displays both the preset $\Delta f$ and the differences $f_o - f$ for the system operation. A manual servo drive potentiometer 31 may be controlled by the operator to override the comparator for manual operation using the display to bring the difference $f_o - f$ to a value equal to $\Delta f$. In either a manual or an automayic mode, a switch 32 is manually operated to turn off the unit 23 when the desired stress is achieved in the bolt. A second switch 33 is momentarily closed to cause the end conditions $(f$ and $f_o - f)$ to be stored along with the starting frequency $(f_o)$ and preset stress $(\Delta f)$. Thereafter, to test the stress of the bolt, the servo drive unit is held off through the switch 32 while the same $\Delta f$ is preset and the system is turned on. To reach a coincidence condition more quickly through the feedback signal, the VCO may be manually adjusted to the previously stored central frequency, $f$. Then the system is allowed to run for a period sufficient for the measured frequency of the oscillator to stabilize. The displayed difference $(f_o - f)$ may then be visually compared with the preset value $\Delta f$ and, if desired, stored by pushing the button 33.

The digital display and recorder 30 includes means for addressing a first bank of memory locations for the storage of data during installation, and for addressing a second bank of memory locations for the storage of subsequent inspection data. In each case of storing data, additional data is manually entered for storage through a keyboard (not shown) to identify the bolt and the date of installation or inspection.

Theoretical considerations of the present invention will now be discussed. The velocity of ultrasonic waves propagating in a structural member, such as an aerospace fastener, is affected by the magnitude of the applied stress. Therefore, although ultrasonic techniques can be used to measure stress related velocity changes when the additional effect of stress related dimensional changes are not present, they are not directly suitable for measurements on structural members that are subject to a dimensional change. Therefore, the present invention is based on measurements calculated on the combined effect of stress, particularly tension, on velocity and length changes. For example, when a fastener is tensioned, the overall length increases by an increment $\Delta L$ and the acoustic velocity changes by an increment $\Delta V$. The acoustic transit time within a fastener is therefore dependent on both $\Delta L$ and $\Delta V$ which are normally of the order of 0.4% and 0.6%, respectively, of bolt length at rated loads. Consequently, the change in transit time is estimated to be in the range of one tenth to one hundredth the transit time of an unloaded fastener. The accurate measurement of time changes in this range requires a measurement method one or two orders of magnitude higher than the accuracy of current ultrasonic measurement techniques that attempt to precisely measure the time between acoustic pulses. Consequently, the present invention is based on a measurement technique capable of meeting the necessary accuracy requirements.

The VCO excitation frequency is initially adjusted to a value $f_o$ such that the received echo pulse $A_2$ is in phase with the received echo pulse $B_1$. If the structural member is now stressed, the phase between the two pulses will change since the travel time for the paired pulses changes due to change in both velocity and travel distance. The VCO frequency is changed to a new value $f$ such that the received echo pulse $A_2$ and the received echo pulse $B_1$ are again in phase. In other words, the frequency of the VCO is adjusted for the same number of wave lengths to occur over the fastener length L as the fastener is stressed.

If the bolt is made to be half the acoustic wavelength, the acoustic travel distance is related to the acoustic properties:

$$\lambda = 2L = v/f$$

$$f = v/2L$$

wherein:
L = Length of fastener
v = Acoustic velocity of the material
f = Pulse repetition rate of excitation pulses
$\lambda$ = Acoustic wavelength
The velocity of acoustic propagation in a fastener is:

$$v = \text{Mod.}/\rho \tag{1}$$

where
Mod. = E for slender, unstressed rod and G for thicker, unstressed rod. (In either case it will change with stress.)
$\rho$ = Density of fastener
E = Young's Modulus
G = Shear Modulus Therefore, the change in repetition rate $\Delta f$ necessary to maintain the same number of acoustic wavelengths in a stressed fastener is:

$$\Delta f = \tfrac{1}{2}(V_1/L_1 - V_2/L_2) \tag{2}$$

and $$2\Delta f = V_1/L_1 - (V_1 - \Delta V/L_1 + \Delta L) \tag{3}$$

A series of experiments have been conducted to determine is $\Delta f$ vs load is linear for a fastener under tensile stress, and whether an empirical description of the relationship would be a more direct method of measurement. The results showed that a specific linear relationship does exist for a given fastener type and size. It is believed that a linear relationship will exist for any structural member, including one under compression.

The indicated ultrasonic data were obtained using the novel pulse pair coincidence technique of the present invention. To implement this technique, the circuit 17 is used to sample a received signal from the ultrasonic transducer after a predetermined time delay to measure the time interval between echo pulses. The problem of accurately determining transist time by measuring the time interval between echo pulses is difficult, and in some instances impossible, due to the reduction in echo pulse amplitude in successive echoes as well as slope changes in the leading edges of the signal after transversing several inches of material. Consequently, it is very difficult to precisely determine where an echo signal begins.

Alternative techniques measure the time interval between component oscillations of the unrectified echo signal. However, serious errors arise because of the possibility of multiple interpretations and interactions between the acoustic signals within the structural member. Additionally, the echo signal components necessarily include a number of frequencies. If the material is highly dispersive within this component frequency bandwidth, the shape of the echo signal oscillations change and can lead to incorrect transit times. Excessive damping of higher frequency components and the presence of pronounced anisotropy conditions change the shape of successive echo signals.

The pulse pair coincidence technique of the present invention provides what is believed a most advanced approach for making precise ultrasonic stress measurements in fasteners and other structural members. The measurements are based on the precision of pulse superposition (coincidence) techniques. Pulse pairs spaced sufficiently far apart in time are used to reduce interference from unwanted acoustic reflections. Thus, absolute stress measurements are made, free of unnecessary interference from unwanted acoustic reflections and independent of any time variations in the acoustic coupling. This provides a measurement system capable of use in either a manual or an automatic mode. The system may be employed, for example, to tighten a number of fasteners to various loaded levels, and then later employed to accurately remeasure the tensile load of each fastener without loss in accuracy.

The system of FIG. 1 will now be described in greater detail in respect to the pulser 14 with reference to FIG. 3, and in respect to the switch 17 and phase sensitive coincidence detector 19 with reference to FIG. 4. The digital timer is comprised of a conventional counter and gates to detect the desired status of the counter for the timing signals required. Once the desired timing signal pattern is established through judicious gating of output stages in the counter, the pattern remains fixed; only the time scale of that pattern is varied as the frequency of the VCO is controlled by the feedback signals. The receiver is also conventional in design, and is comprised of several amplifier stages with appropriate bandpass filtering to minimize noise. The input of the first stage is diode limited by two parallel diodes connected with opposite polarity to ground so that echo return signals received will be amplified, while pulses transmitted by the pulser are limited to the voltage drop across the diodes (e.g. ± 0.7 volt) to protect the receiver components against the high amplitude pulse being transmitted.

Referring now to FIG. 3, a 500 pf storage capacitor $C_1$ is charged to a high voltage (e.g., +200 volts) while a transistor $Q_1$ is held off. When the digital timer emits a short pulse of a pulse pair, transistors $Q_1$ and $Q_2$ are turned on to connect the positive side of the storage capacitor to circuit ground, thus discharging the capacitor through a series diode $D_1$ and the ultrasonic transducer in 5 to 10 nanoseconds. The transistor $Q_1$ is an avalanche transistor that can discharge the capacitor in that time with high current (20 amps). The result is a short, high amplitude negative pulse transmitted to the transducer 13 (FIG. 1).

The second transmitted pulse in a pulse pair may occur less than 10 microsecnds after the first. It is necessary to quickly recharge the pulser circuit and replace the expended energy. The digital timer allows four tenths of the interval between pulses for the avalanche transistor $Q_1$ to cut off completely and regain full switching control. This period would be 4 microseconds out of a 10 microsecond interval. Transistor $Q_3$ then causes a pair of transistors $Q_4$ and $Q_5$ to conduct for another four tenths of the interval (4 microseconds). Conduction of that pair of transistors shunts a resistor $R_1$ to permit faster charging of the capacitor from a source (+V) through a zener diode $Z_1$, resistor $R_2$ and a shunt diode $D_2$ to circuit ground. The transistors $Q_3$ through $Q_5$ are then turned off again for two tenths of the interval (or 2 $\mu$sec) before the next trigger pulse of a pair. During that period, the capacitor $C_1$ is maintained charged through the resistor $R_1$ and a smaller resistor $R_2$. The latter is nominally only 820 ohms, while the resistor $R_1$ is 270 K ohms for a storage capacitor of 500 pf. A 150 pf filter capacitor $C_2$ limits the minimum rise time on the charging current.

The nominal or central frequency is assumed to be 100 KHz in the foregoing discussion for a fastener approximately 1¼ inches long. The exact frequency will depend upon the particular fastener. In practice, the central frequency may be adjusted at the VCO manually. Once so adjusted, the system will track the effective length of the fastener as it is tightened (or loosened) through the operation of the phase sensitive detector 19 which will be described with reference to FIG. 4.

Figure 4:
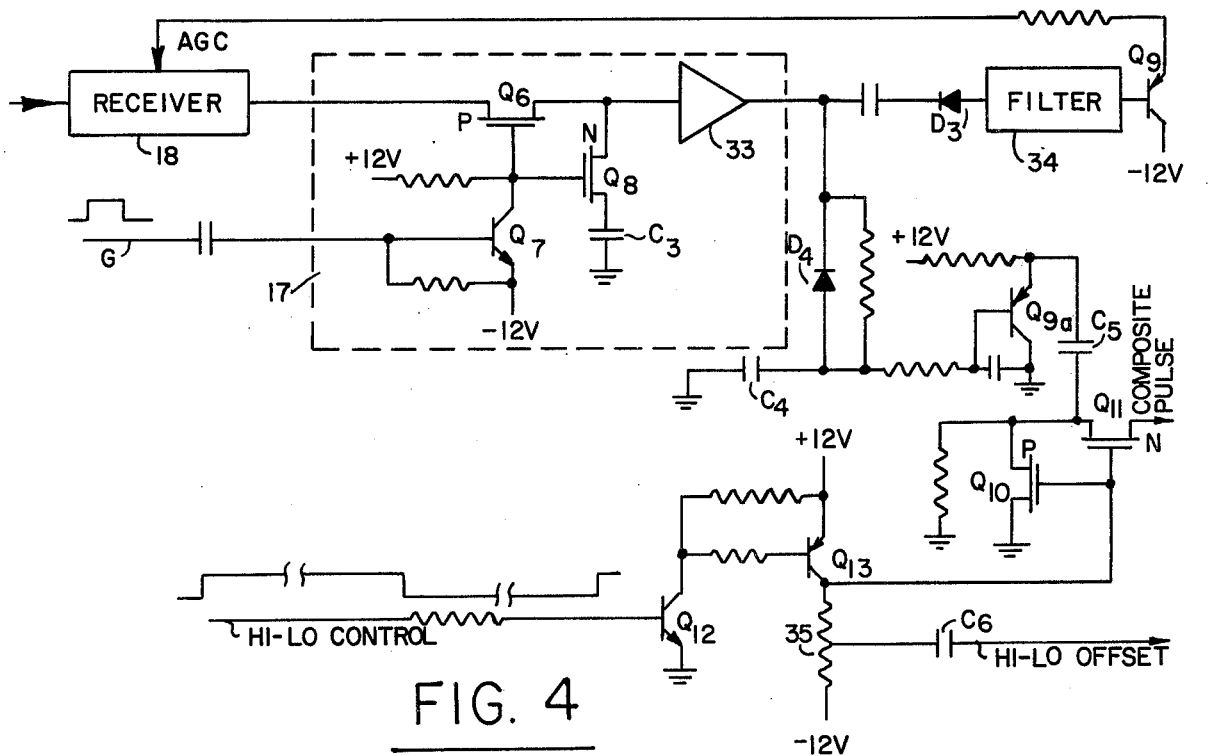
FIG. 4 is a diagram of a circuit for a phase sensitive coincidence detector in the system of FIG. 1.

Referring now to FIG. 4, the output of the receiver 18 is periodically coupled by a P-channel field-effect transistor $Q_6$ to an amplifier 33 by each gate pulse G applied to the base of a transistor $Q_7$ at a time when each composite echo return $A_2 + B_1$ is expected, as noted hereinbefore with reference to FIG. 2. At all other times the transistors $Q_6$ and $Q_7$ are turned off, and an N-channel transistor $Q_8$ is turned on to shunt the output of the receiver to circuit ground, thus eliminating any noise from the system while waiting for the next composite pulse. A capacitor $C_3$ is employed to isolate the DC reference of the amplifier input from circuit ground in order that it respond quickly to the receiver output when the transistor $Q_6$ is turned on.

The composite pulse $A_2 + B_1$ for the return signal $R_{A+B}$ is shown in FIG. 2 for the ideal phase coincidence condition between the pulse $A_2$ for the second echo return of the first of a pulse pair and the pulse $B_1$ for the first echo return of the second of the pulse pair. The ideal composite pulse is rarely received for reasons that will become apparent from the following discussion, but the general shape will be as as for the ideal composite pulse; only the pulse width and height will vary to produce greater width and lower amplitude as the time of the echo pulse $A_2$ deviates from the time of the echo pulse $B_1$. Since the central frequency of the VCO is to be adjusted to maintain virtual coincidence of the echo pulses $A_2$ and $B_1$, the pulse width and height of the composite pulse will remain substantially constant over a number of samples. Consequently, the sampled composite pulses (inverted by the amplifier 33) can be rectified by a diode $D_3$ and filtered by a lowpass filter 34 to provide automatic gain control (AGC) for the receiver 18 via a transistor $Q_9$ as shown. However, AGC is not essential for the system as shown in FIG. 1.

The output of the switch 17 is also rectified and filtered in the phase sensitive coincidence detector 19 by a diode $D_4$ and integrating capacitor $C_4$. The detected and integrated composite pulses are coupled by a transistor $Q_{9a}$ and a capacitor $C_5$ to a pair of field effect transistors $Q_{10}$ and $Q_{11}$ alternately turned on and off by the digital timer 15 via transistors $Q_{12}$ and $Q_{13}$. While the transistors $Q_{12}$ and $Q_{13}$ are held on by a high signal from the digital timer for a number (typically 5) of composite pulse samples, the P-channel field-effect transistor $Q_{10}$ is held off while the N-channel field-effect transistor $Q_{11}$ is held on, thus coupling the input terminal of the operational amplifier 20 (FIG. 1) to the capacitor $C_5$. When the symmetrical square wave timing signal from the digital timer is low, the transistor $Q_{10}$ is held on and the transistor $Q_{11}$ is held off, thus connecting the capacitor $C_5$ to circuit ground.

The symmetrical square wave from the digital timer is also coupled by a potentiometer 35 and capacitor $C_6$ to the VCO as a HI-LO OFFSET signal as shown in FIG. 1. Consequently, the VCO is first driven high for a number (5) of pulse-pair cycles, and then low for the same number of cycles, to shift the echo pulse $B_1$ first to the left and then to the right of the echo pulse $A_2$. If the center frequency is correct, the out-of-phase condition will be the same in both cases to produce a wider and lower amplitude composite pulse. Consequently, as the capacitor $C_5$ is switched between circuit ground and the input terminal of the operational amplifier 20 (FIG. 1), the net charge across the capacitor will remain the same. (Note that the feedback capacitor 21 on the operational amplifier 20 maintains its input terminal at virtual ground potential.) If the voltage is first −4 volts for the low oscillator frequency and then −6 volts for the high oscillator frequency offset, there will be a net of −2 volts DC shift on the HI-LOW OFFSET signal through the amplifier 20 to increase the center frequency of the VCO. Conversely, if the voltage is first −6 volts and then −4 volts, there will be a net +2 volts DC shift on the HI-LOW OFFSET signal through the amplifier 20 to decrease the center frequency of the VCO. Once the HI-LOW OFFSET is shifted to produce the proper center frequency in the VCO, the voltage will be −5 volts for both the high and the low oscillator frequency, and the shift of the HI-LOW OFFSET will be zero. In that manner, the HI-LOW OFFSET synchronized with the switching of the coupling capacitor $C_5$ between the input of the operational amplifier and ground produces phase sensitive detection of any error in coincidence between the second echo $A_2$ of the first pulse and the first echo $B_1$ of the second pulse of a pulse pair while tracking in frequency the correct center frequency for the load condition of the fastener. It should be noted that while the VCO output is varying between high and low, the frequency counter 22 is determining the center frequency by averaging over a sufficient number of cycles of the HI-LOW OFFSET signal. The measured center frequency, $f$, is thus a measurement of the effective length of the fastener, and the difference between that frequency and the initial frequency, namely $f_o - f$, is an accurate measurement of the fastener load if $f_o$ is the center frequency measured for a no-load condition of the fastener.

From the foregoing, it is evident that the present invention permits interferometric readings in an ultrasonic system while minimizing multiple reflections in the member being measured or inspected. It detects the optimum phase between coincident echo pulses of a pulse pair and automatically controls the VCO to the correct frequency. The technique is based upon coincidence matching of echo pulses from a pulse pair reflected from an internal surface of the member as distinct from trying to measure the time from a transmitted pulse to the return of an echo pulse received. To enhance the process of phase sensitive coincidence detection, the echo pulses being matched are gated, but it is not necessary for an operator to adjust the gate pulse position. The adjustment of the VCO for the dual pulse operation automatically adjusts the gate pulse position.

Although a particular embodiment of the invention has been described and illustrated herein with reference to a fastener, and in particular a bolt, it is to be understood that the method and apparatus of the invention may be used to equal advantage for measuring the dimensional or stress change of any structural member, particularly a member under stress, provided only that an acoustic pulse may be transmitted into it at one end and reflected from its other end in the direction of the dimension of interest. The member might even be a pressure vessel, such as a nuclear pressure vessel with high pressure inside or a submarine with high pressure outside subjecting the vessel wall to high stress levels. It would only be necessary to locate or otherwise provide for transmitting an ultrasonic pulse through the wall for reflection of echos back from the other side of the transducer. It should also be recognized that modifications and equivalents may readily occur to those skilled in the art. Consequently, it is intended that the claims be interpreted to cover such modifications and equivalents.

What is claimed is:

1. An ultrasonic method for measuring dimensional change of a structural member comprising the steps of
timing the generation of paired acoustic pulses transmitted into said member at one end for reflection from its other end in a path along the direction in which dimensional change is to be measured, said timing being controlled by a variable oscillator adjusted for coincidence between the second reflection received at said one end of the first pulse of a pair with the first reflection received of the second pulse of said pair,
measuring the frequency $f_o$ of said oscillator for the condition of reflected pulse coincidence with no dimensional change in said member, and storing the frequency $f_o$ for comparison,
measuring the frequency $f$ of said oscillator for the condition of reflected pulse coincidence with a dimensional change in said member, and
determining the difference between said frequency $f_o$ and said frequency $f$ as a measure of the extent of said dimensional change.

2. A method as defined in claim 1 wherein said variable frequency oscillator is continually adjusted while determining said frequency $f$ and while said member is undergoing said dimensional change, and continually determining said difference between said frequency $f_o$ and said frequency $f$.

3. A method as defined in claim 2 including the predetermination of a desired dimensional change to said member in terms of change of frequency, $\Delta f$, from said frequency $f_o$, continually comparing said difference, $f_o - f$, with said predetermined change of frequency, $\Delta f$, while said member is undergoing dimensional change, and terminating the process of subjecting said member to dimensional change when said difference $f_o - f$ is substantially equal to said predetermined change of frequency $\Delta f$.

4. A method as defined in claim 1 wherein detecting the condition of reflected pulse coincidence between the second reflection received from the first pulse of a pulse pair and the first reflection received from the second pulse of a pulse pair is accomplished by alternately offsetting the frequency of said oscillator a predetermined amount above and below a frequency which produces said coincidence condition, the offset in each direction being held for a predetermined number of pulse pair cycles, continually producing a signal proportional to the amplitudes of the composite pulses of said second reflection received from the first pulse and said first reflection received from the second pulse of each pair during successive high and low offset intervals, continually integrating the difference between the amplitude of said signal during a high offset interval and the amplitude of said signal during an adjacent low offset interval to produce a phase-sensitive error signal proportional to the extent of the phase difference between pulses of said composite pulses, and continually adjusting the frequency of said oscillator in a direction to reduce said error signal toward zero, whereby the central frequency of said oscillator continually varies in proportion to said dimensional change.

5. An ultrasonic method for measuring a dimension of a structural member comprising the steps of
timing the generation of paired acoustic pulses transmitted into said member at one end for reflection from its other end in a path along the direction in which dimension is to be measured, said timing being controlled by a variable oscillator adjusted for coincidence between the second reflection received at said one end of the first pulse of a pair with the first reflection received of the second pulse of said pair,
determining the frequency $f_o$ of said oscillator for the condition of reflected pulse coincidence in said member of predetermined dimension in said member, measuring the frequency $f$ of said oscillator for the present condition of reflected pulse coincidence in said member, and determining the difference between said frequency $f_o$ and said frequency $f$ as a measure of the change of said dimension relative to said predetermined dimension.

6. An ultrasonic method for measuring stress of a structural member comprising the steps of timing the generation of paired acoustic pulses transmitted into said member at one end for reflection from its other end in a path along the direction in which stress is to be measured, said timing being controlled by a variable oscillator adjusted for coincidence between the second reflection received at said one end of the first pulse of a pair with the first reflection received of the second pulse of said pair, measuring the frequency $f_o$ of said oscillator for the condition of reflected pulse coincidence with no stress in said member, and storing the frequency $f_o$ for comparison, measuring the frequency $f$ of said oscillaator for the condition of reflected pulse coincidence with a stress in said member, and determining the difference between said frequency $f_o$ and said frequency $f$ as a measure of the extent of said stress.

7. A method as defined in claim 6 wherein said variable frequency oscillator is continually adjusted while determining said frequency $f$ and while said member is undergoing said stress, and continually determining said difference between said frequency $f_o$ and said frequency $f$.

8. A method as defined in claim 7 including the predetermination of a desired stress to said member in terms of change of frequency, $\Delta f$, from said frequency $f_o$, continually comparing said difference, $f_o-f$, with said predetermined change of frequency, $\Delta f$, while said member is being subjected to changing stress, and terminating the process of subjecting said member to changing stress when said difference $f_o-f$ is substantially equal to said predetermined change of frequency $\Delta f$.

9. A method as defined in claim 6 wherein detecting the condition of reflected pulse coincidence between the second reflection received from the first pulse of a pulse pair and the first reflection received from the second pulse of a pulse pair is accomplished by alternately offsetting the frequency of said oscillator a predetermined amount above and below a frequency which produces said coincidence condition, the offset in each direction being held for a predetermined number of pulse pair cycles, continually producing a signal proportional to the amplitudes of the composite pulses of said second reflection received from the first pulse and said first reflection received from the second pulse of each pair during successive high and low offset intervals, continually integrating the difference between the amplitude of said signal during a high offset interval and the amplitude of said signal during an adjacent low offset interval to produce a phase-sensitive error signal proportional to the extent of the phase difference between pulses of said composite pulses, and continually adjusting the frequency of said oscillator in a direction to reduce said error signal toward zero, whereby the central frequency of said oscillator continually varies in proportion to said change in stress.

10. A method for measuring the ultrasonic transit time of a pulse through a structural member without regard to the transit time through coupling media comprising the steps of double pulsing an ultrasonic transducer coupled to a structural member at a pulse pair rate adjusted so that the second reflected echo of the first pulse of a pair coincides with the first reflected echo of the second pulse of the pair, whereby the pulse rate so adjusted is an accurate measure of the round trip transit time of an ultrasonic pulse through said member.

11. Apparatus for measuring dimensional change of a structural member comprising a signal controlled variable oscillator, means for timing the continual generation of paired acoustic pulses transmitted into said member at one end for reflection from its other end in a path along the direction in which dimensional change is to be measured, said timing means being controlled by said variable oscillator to produce said paired pulses at an interval for coincidence between the second reflection of the first pulse of a pulse pair received at said one end with the first reflection of the second pulse of said pulse pair received at said one end, phase sensitive coincidence detection means for detecting any phase difference between the second reflection of the first pulse of said pulse pair with the first reflection of said second pulse of said pulse pair and for producing said signal proportional to any phase difference detected, means for applying said signal to said oscillator to reduce any phase difference detected toward zero, means for storing an initial frequency $f_o$ of said oscillator for the condition of reflected pulse coincidence with no dimensional change in said member, means for measuring the frequency $f$ of said oscillator for the condition of reflected pulse coincidence with a dimensional change in said member, and means for determining the difference between said frequency $f_o$ and said frequency $f$ as a measure of the extent of said dimensional change.

12. Apparatus as defined in claim 11 including operational means for subjecting said structural member to a dimensional change, means for storing a desired dimensional change in terms of change of frequency from said initial frequency $f_o$, means for continually comparing said difference, $f_o-f$, with said predetermined change of frequency while said member is undergoing dimensional change, and means for terminating the operation of said means for subjecting said member to dimensional change when said difference $f_o-f$ is substantially equal to said predetermined change of frequency.

13. Apparatus as defined in claim 11 wherein said phase sensitive coincidence detection means for detecting the condition of reflected pulse coincidence between the second reflection received from the first pulse of a pulse pair and the first reflection received from the second pulse of a pulse pair includes means for alternately offsetting the frequency of said oscillator a predetermined amount above and below a frequency which produces said coincidence condition, the offset in each direction being held for a predetermined number of pulse pair cycles, means for forming the composite pulses of said second reflection received from the first pulse and said first reflection received from the second pulse of each pair during successive high and low offset intervals, and means for continually integrating the difference between the amplitude of said composite pulses during successive high and low offset intervals to produce a phase-sensitive error signal proportional to the extent of the phase difference between reflected pulses received to form said composite pulses.

14. Apparatus for measuring a dimension of a structural member comprising a signal controlled variable oscillator, counting means for timing the continual generation of paired acoustic pulses by counting cycles of said variable oscillator, means for transmitting said paired acoustic pulses into said member at one end for reflection from its other end in a path along the direction in which dimension is to be measured and for receiving reflected pulses at said one end, means for controlling said variable oscillator for coincidence between the second reflection received of the first pulse of a pair with the first reflection received of the second pulse of said pair, and means for determining the frequency of said oscillator for the condition of reflected pulse coincidence in said member as a measure of dimension of said member.

15. Apparatus as defined in claim 14 including means for storing the frequency of said oscillator for the condition of reflected pulse coincidence in said member for comparison after said member has undergone a change in dimension, and means for determining the difference between said stored frequency and a present frequency as a measure of the change of said dimension relative to said predetermined dimension.

16. Apparatus for measuring stress of a structural member comprising a controlled variable oscillator, means responsive to said oscillator for continually generating a timed pair of acoustic pulses, means for transmitting said paired acoustic pulses into said member at one end for reflection from its other end in a path along the direction in which stress is to be measured and for receiving at said one end reflections of said acoustic pulses from said other end, phase control means for continually controlling the frequency of said oscillator to continually adjust the time between acoustic pulses of each pair for coincidence between the second reflection received at said one end of the first pulse of a pair with the first reflection received at said one end of the second pulse of said pair by a feedback signal, means for measuring the frequency $f_o$ of said oscillator for the condition of reflected pulse coincidence with no stress in said member, and storing the frequency $f_o$ for comparison, means for measuring the frequency $f$ of said oscillator for the condition of reflected pulse coincidence with a stress in said member, and means determining the difference between said frequency $f_o$ and said frequency $f$ as a measure of the extent of said stress.

17. Apparatus as defined in claim 16 including stressing means for applying continually changing stress to said member, means for storing a desired stress to be applied by said stressing means to said member in terms of change of frequency from said frequency $f_o$, means for continually comparing said difference, $f_o - f$, with said predetermined change of frequency, while said member is being subjected to changing stress, and means for terminating the operation of said stressing means subjecting said member to changing stress when said difference $f_o - f$ is substantially equal to said predetermined change of frequency.

18. Apparatus as defined in claim 16 wherein said phase control means includes means for detecting the condition of reflected pulse coincidence between the second reflection received from the first pulse of a pulse pair and the first reflection received from the second pulse of a pulse pair, said detecting means comprising means for alternately offsetting the frequency of said oscillator a predetermined amount above and below a frequency which produces said coincidence condition, the offset in each direction being held for a predetermined number of pulse pair cycles, means for continually producing composite pulses of said second reflection received from the first pulse and said first reflection received from the second pulse of each pair during successive high and low offset intervals, means for continually integrating the difference between the amplitude of said composite pulses during successive high and low offset intervals to produce a phase-sensitive error signal proportional to the extent of the phase difference between constituent pulses of said composite pulses, and means for applying said phase-error signal to said oscillator in a direction to reduce said error signal toward zero, whereby the central frequency of said oscillator continually varies in proportion to said change in stress.

* * * * *